United States Patent [19]

Schultz et al.

[11] Patent Number: 5,051,252

[45] Date of Patent: Sep. 24, 1991

[54] OXIDIZING MIXTURES FOR HAIR CARE USE

[75] Inventors: Thomas M. Schultz, Highland Mills, N.Y.; Eva Day, Stamford, Conn.

[73] Assignee: Shiseido Co. Ltd., Tokyo, Japan

[21] Appl. No.: 562,611

[22] Filed: Aug. 3, 1990

[51] Int. Cl.$^5$ .......................... A61K 7/09; A61K 7/11; A45D 7/04

[52] U.S. Cl. ...................................... 424/71; 132/204; 132/209; 424/72

[58] Field of Search ...................... 424/62, 72, 71, 613, 424/616, 661, 665; 252/186.21, 186.25, 186.28, 186.36, 186.37, 187.2, 187.23; 514/769, 771; 132/204, 209

[56] References Cited

U.S. PATENT DOCUMENTS

| | | | |
|---|---|---|---|
| Re. 23,218 | 4/1950 | Levy et al. | 252/187.23 X |
| 2,358,866 | 9/1944 | MacMahon | 252/187.23 X |
| 2,780,579 | 2/1957 | Schwarz et al. | 424/71 X |
| 2,899,965 | 8/1959 | McGoldrick et al. | 424/71 X |
| 3,580,851 | 5/1971 | Heid et al. | 252/186.36 X |
| 4,776,857 | 10/1988 | Carroll et al. | 424/63 X |
| 4,861,514 | 8/1989 | Hutchings | 252/187.21 |

*Primary Examiner*—Thurman K. Page
*Assistant Examiner*—Susan S. Rucker
*Attorney, Agent, or Firm*—Melvin I. Stoltz

[57] ABSTRACT

By combining an aqueous chlorite solution with an organic or inorganic buffer salt and a divalent metal ion, a stable aqueous chlorite solution is attained for use in substantially improving the durability and resulting visual appearance of permanently waved hair. In addition, the present invention is equally effective as a post treatment for freshly permanently waved hair or as the oxidizer in the permanent waving process. Furthermore, this aqueous chlorite solution can be intermixed with conventional oxidizers to attain the desirable beneficial results.

23 Claims, No Drawings

OXIDIZING MIXTURES FOR HAIR CARE USE

TECHNICAL FIELD

This invention relates to permanent waving compositions and, more particularly, to novel oxidizing mixtures used in conjunction with permanent waving compositions for imparting a permanent wave to the hair.

BACKGROUND ART

It is well known that hair is composed of a unique protein material called "keratin", which is distinguished by the fact that it contains a very significant amount of an amino acid (cystine) which contains the element sulfur in addition to the elements nitrogen, oxygen, carbon and hydrogen. In the natural synthesis of hair, the element sulfur covalently links intra or inter polypeptide chains (K) through two sulfur atoms (S—S) to give keratin protein (K—S—S—K). Only by chemical action can this covalent linkage be broken.

In this regard, many prior art compositions have been developed for the "cold permanent waving" of hair. Typically, these prior art systems treat the hair with a reducing agent which breaks the disulfide (cystine) linkage in the hair while the hair is wound around a curling rod.

In general, permanent hair waving is usually carried out by subjecting the hair to reagents containing a free—SH group or thiol. These materials are also called mercaptans. In this treatment, the hair usually is either wrapped on the rods with water or the lotion containing the thiol, and then saturated with thiol lotion. The thiol waving agent acts to break the disulfide bonds within the hair fiber forming thiol groups in the hair protein and disulfide bonds between two thiol waving agent molecules. The chemistry involved in the reaction of the mercaptan with the cystine disulfide bonds in the hair fiber is illustrated by the following chemical equations:

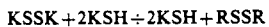

$$KSSK + 2KSH \rightleftharpoons 2KSH + RSSR$$

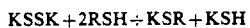

$$KSSK + 2RSH \rightleftharpoons KSR + KSH$$

When a sufficient number of hair disulfide bonds have been broken, the hair is realigned to pair previously unpaired hair protein thiol groups opposite each other. At this point, the hair is rinsed, removing the unreacted thiol waving agent and disulfide reaction product formed from it. Then, the hair is saturated with an oxidizing agent, or neutralizer, such as hydrogen peroxide or bromate salt, to reform disulfide bonds between the newly paired hair protein thiols, thereby giving the hair a new configuration or wave, or adding curl to the hair. By rebonding the sites of the reduced keratin in their new curled configuration, a permanent set which is impervious to water is established.

Much of the rebonding of the reduced sites is accomplished by the action of the chemical oxidizing agent, which is typically hydrogen peroxide and can be illustrated by the following chemical reaction:

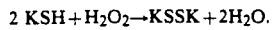

$$2 KSH + H_2O_2 \rightarrow KSSK + 2H_2O.$$

In the art of permanent waving, there is much trial and error, with the hair being over-processed, in some instances. The characteristics of over-processing are raspy feel to the hair or a bleaching of the natural underlying color. Structural evaluation of the hair fiber by instrumentation usually reveals that the structural integrity of the hair is lessened, which is evidenced by either an increase in the amount of cysteine and cystic acid or a lessening of the cystine content relative to the hair not so processed.

Some detrimental effect to hair fiber is unavoidable, as the process of permanent waving involves controlled bond scission of the disulfide linkages within the keratin proteins. Recovery of these disulfides is the determining factor for the tightness of the curls and overall tensile strength.

For these reasons, improved oxidizing agents or neutralizers which might be more efficient in reforming the disulfide bonds is constantly being sought. The typical oxidizing agents used in the art of hair care are hydrogen peroxide and the alkali metal and ammoniated salts of bromate, persulfate and carbonates. However, these conventional oxidizing agents typically exhibit such disadvantages as the bleaching of the hair, skin irritation and instability in solution.

In an attempt to eliminate these prior art difficulties and drawbacks typically encountered with the oxidizing or neutralizing agents, attention has been paid to chlorite, chlorite salts, and aqueous solutions of chlorite.

First, these aqueous solutions tend to decompose to the other equilibrium species of hypochlorous acid that is, hypochlorite and chlorine dioxide. Both of these chemicals damage the cuticle and other components of hair with the net result that the hair takes on the appearance of being "damaged", e.g., there may be a raspy feel to the hair and even some degree of lightening. Second, and of more serious concern, is that both hypochlorite and chlorine dioxide can irritate skin more so than either hydrogen peroxide, persulfate, or bromate.

U.S. Pat. No. 3,265,582 teaches that salts: of chlorate and perchlorate are capable of oxidizing hair which had been previously relaxed and so imparting a wave to the hair. The solutions so described are aqueous. German Patent No. 2,039,358 describes the use of chlorates to affect the color formation of standard oxidation dyes to color the hair and by doing so establishes that variants of hypochlorous acid in the lower oxidation states are indeed applicable to the art of hair care. More recently, U.S. Pat. No. 4,776,857 introduced the use of perhalosalts, perchlorates included, to affect the in-situ condensation of indole derivatives also for the exclusive effect of coloring the hair. Unfortunately, there is the severe drawback to use of such oxychlorine salts in that they are typically unstable in water and must therefore be mixed immediately prior to use and more so, the solutions are irritating to skin.

In U.S. Pat. No. 2,899,965, the use of specifically aqueous chlorite, preferably, derived from sodium chlorite as the oxidizing agent in a permanent wave solution, is discussed. However, in addition to describing the advantages of chlorite, the undesirable features associated with chlorite compositions are also fully discussed. In particular, the chlorite solutions were used by working through the hair after unwinding from the roller followed by rewrapping. Chlorite compositions can explode into flames or cause organic materials to spontaneously combust when brought in contact with reductants such as thioglycolic acid, especially if the combinations were allowed to dry. In an attempt to overcome these extremely detrimental properties, which rendered such chlorite inapplicable for commercial use, additives such as urea and sodium lactate were disclosed.

It has been demonstrated that aqueous solutions of chlorite can convert mercaptans into disulfides, and hence, in the process of permanent waving, thereby neutralize a permanent wave solution to impart a wave to hair [see, for example, T. Ruemele in Kosmetic; Vol. #23; pp. 695-696; (1957); and K. Plouch and D. Dziewonska: Roc. Chemi Ann. Soc. Chim.; Vol. 41; pp. 1285-1289; (1967)]. In Kosmetic, the use of aqueous sodium chlorite is discussed for permanent waving. In that discussion, the concentration of chlorite, which was generated in-situ, is estimated at 4% to 10%. However, these earlier experiments suggested that there were several problems associated with the use of this material in purely aqueous media.

In U.S. Pat. No. 2,780,579, the use of chlorite in association with ascorbic acid to produce dehydroasorbic acid using sodium chlorite as well as other conventional oxidizing compounds is provided.

Although substantial effort has been expended in developing commercially employable oxidizing mixtures or neutralizers, it is clearly apparent that prior art systems have failed to develop a chlorite based oxidizing mixture which is easy to produce, store and use. Typically, the prior art problems detailed in the patents identified above have continued and have been incapable of being eliminated, prior to the present invention.

Therefore, it is a principal object of the present invention to provide a chlorite based solution which attains the advantages well known for chlorite solutions, without experiencing any of the difficulties and drawbacks previously encountered with chlorite solutions.

Another object of the present invention is to provide a chlorite based solution having the characteristic features described above which can be formulated inexpensively and used widely without any detrimental effects.

Another object of the present invention is to provide a chlorite based solution having the characteristic features described above which can be employed as a neutralizer or an oxidizer in the permanent waving of hair.

Another object of the present invention is to provide a chlorite based solution having the characteristic features described above which can be used as an additive to commercially available oxidizers or neutralizers.

A further object of the present invention is to provide a chlorite based solution having the characteristic features described above which can be employed as a post treatment for permanently waved hair.

Other and more specific objects will in part be obvious and will in part appear hereinafter.

DETAILED DESCRIPTION

In order to overcome the prior art difficulties and drawbacks previously encountered with employing chlorite as the oxidizing mixture or neutralizer in a permanent waving procedure, it has been found that an aqueous solution of chlorite can be successfully stabilized by combining therewith a divalent metal ion and an organic or inorganic buffer salt.

In the preferred embodiment, the chlorite comprises an alkali metal, ammonium, or organo ammonium chlorite salt, with sodium chlorite being preferred. In addition, the buffer salts comprise the alkali metal salts of citric acid, tartaric acid, ethylene tetra-acetoxylamine or acetylacetone. Finally, the divalent metal ion preferably comprises one selected from the group consisting of zinc, copper, magnesium, and manganese.

In order to obtain a stable solution, it has been found that the aqueous chlorite solution of the present invention preferably comprises between about 0.001% and 10.0% by weight of the divalent metal ion, between about 0.01% and 20.0% by weight of the organic or inorganic buffer salt, and between about 0.001% and 8.0% by weight of the alkali metal, ammonium or organo ammonium chlorite salt. More particularly, it has been found that a stable aqueous chlorite solution is obtained by employing between about 0.4% and 6.0% by weight of sodium chlorite, between about 1.2% and 12.0% by weight of the divalent metal ion, and between about 1.2% and 12.0% by weight of the organic or inorganic buffer salt. The resulting composition is preferably diluted in water at a ratio ranging between 1 and 30.

In the preferred formulations, sodium chlorite is employed as the chlorite salt and tribasic sodium citrate is preferably employed as the buffer salt. In addition, the divalent metal ion is provided by incorporating at least one water soluble salt of a divalent metal ion selected from the group consisting of magnesium sulfate, magnesium chloride, copper sulfate, copper chloride, magnesium chloride hexahydrate, zinc chloride hydrate, zinc sulfate, and zinc chloride.

It has also been found that the chlorite composition of the present invention has a half-wave oxidation potential of 0.65 eV whereas the chemicals typically used in the prior art, eg. bromates and hydrogen peroxide possess half wave-oxidation potentials above 1.2 eV. While this phenomenon cannot be directly correlated with specific reactivity to only those components within the hair that are reformed during the so-called neutralization step, it has been found that the recovery of disulfide structures in the hair is vastly better than the recovery typically achieved when hydrogen peroxide is employed; examples are detailed below.

Furthermore, by employing the chlorite solution of the present invention, a stable, aqueous oxidizing mixture is attained which can be maintained at a neutral pH range by the use of the desired buffers either alone, or in combination, with materials such as ascorbic acid or bromate, typically employed in various hair care applications. The resulting solutions remain exceptionally stable and perform exceptionally well as the oxidizing mixture or neutralizer.

In the compositions employing ascorbic acid, it has been found that the chlorite composition transforms the ascorbic acid to dehydroascorbic acid which then acts as the oxidizing component. Although U.S. Pat. No. 2,780,597, discussed above, reveals the reaction of hydrogen peroxide with ascorbic acid to get dehydroascorbic acid for use as a permanent waving neutralizer, various disadvantages have been realized in using hydrogen peroxide to oxidize the ascorbic acid. In particular, the ascorbic acid solid must be added to the peroxide solution and then mixed thoroughly prior to use and, even then, conversion to dehydroascorbic acid by the hydrogen peroxide has been found to be only moderately efficient. However, by employing the chlorite solutions of the present invention, essentially 100% conversion of ascorbic acid to its dehydro form is realized.

By employing the aqueous chlorite solution of the present invention, stable solutions are obtained which perform excellently as oxidants in the practice of permanently waving hair. Furthermore, if desired, these mixtures can be admixed with carbohydrates to affect a highly durable, reconstruction of the hair after contact with the usual mercaptan species, employed for hair relaxation. In this way, a highly effective and substantially improved permanent wave composition is attained.

BEST MODE FOR CARRYING OUT THE INVENTION

In order to substantiate the versatility of the present invention, the following examples are presented detailing the various aspects of this invention and the ability for chlorite solutions of the present invention to be employed in the art of hair cosmetics, in general, and in the art of permanent waving, in particular. These examples are intended as a teaching of the best mode for carrying out the present invention and are not intended to limit, in any manner, the breadth of this discovery.

Chlorite Solutions as a Post Treatment

We have found that by employing the chlorite solutions of the present invention to freshly permanent waved hair, substantially improved curl retention is realized. As detailed in the following illustrative examples, a longer lasting, tighter curl was attained when the chlorite containing solutions of the present invention were employed as a post permanent waving treatment.

In order to prove the curl retaining efficacy of the present invention, a tress of brown hair of approximately 0.1 to 3 grams with a total length of 15 centimeters was wetted with water and wrapped about a small plastic permanent wave rod. The hair was then thoroughly wetted with a typical permanent wave reducing solution, such as detailed in Table I.

TABLE I

| | |
|---|---|
| Glycerol-monothioglycolate (5% solution) | 280 g |
| Ammonium hydroxide | 40 g |
| Diammonium-dithiodiglycolate | 30 g |
| Water | 850 g |

The hair was then placed in a plastic wrapper and warmed to 50° C. for twenty minutes, followed by copious rinsing with tap water. Next, the wrapped hair was wetted with 2% $H_2O_2$ at pH 4, the pH being obtained by the additional phosphoric acid to a solution of 50% $H_2O_2$ suitably diluted with deionized water. After a period of five minutes, the hair was then wetted with the chlorite solution "A" detailed in Table II.

TABLE II

| | Solutions | | | | |
|---|---|---|---|---|---|
| Ingredients (grams) | A | B | C | D | E |
| Sodium Chlorite | 4 | 4 | 4 | 5 | 5 |
| Tribasic Sodium Citrate | 18 | 18 | 18 | 18 | 18 |
| Magnesium Chloride | 7 | | | | |
| Magnesium Sulfate | | 7 | | | |
| Zinc Chloride Hydrate | | | 7 | | |
| Copper Sulfate | | | | 6 | |
| Magnesium Chloride Hydrate | | | | | 6 |
| Urea | | | | | 50 |
| Hydroxyethyl Cellulose | | | | | 1 |
| Water | 1,000 | 1,000 | 1,000 | 1,000 | 1,000 |

After thorough rinsing, the hair was free of the typical odor associated with the thio component of the permanent wave solution. In addition, after drying and subsequent shampooing, the hair had a fresh odor.

The resulting curl was compared to an identically curled hair sample which had not been post treated with the chlorite solution of this invention. It was found that the curl having the chlorite solution post treatment was tighter and was retained for a substantially longer time period as detailed below.

After six separate cycles of hand shampooing, rinsing and air drying, the permanent waved hair that was post treated with solution "A" of Table II retained its degree of curl longer than the hair sample which did not have the post treatment.

In order to further corroborate the efficacy of the present invention, chlorite solutions "B", "C", "D" and "E" detailed in Table II were individually prepared and applied to a brown hair sample as detailed above in reference to solution "A". All of the steps detailed above were carried out equally for each of these other solutions and compared to the hair sample to which no post treatment application was made.

In each of the samples treated with one of the chlorite solutions detailed in Table II, substantially improved curl retention was attained, even after six separate cycles of hand shampooing, rinsing, and air drying. As was clearly evident from the results observed, each of the chlorite solutions of this invention substantially improve the appearance, permanence and durability of permanently waved hair.

In preparing each of the solutions detailed in Table II, it was found to be most expeditious to prepare the stable chlorite solution by adding 18 grams of the tribasic sodium citrate to one liter of deionized water and stirring until completely dissolved. Then, the appropriate amount of the desired metal ion salt is added in order to form the particular solution desired. Finally, the desired amount of sodium chlorite is added, resulting in a clear solution. In addition, it was also found that all the solutions detailed in Table II remained stable over several months at temperatures ranging between 0° and 60° C.

It is interesting to note that prior art patents, such as U.S. Pat. No. 4,861,514, teach that chlorite compositions may be thickened with various cellulose derived gels or gums in order to intentionally form chlorine dioxide. However, we have found that the addition of the metal ion salt effectively prevents the formation of the chlorine dioxide.

The discovery of the present invention enables stable chlorite solutions to be formed while also incorporating between about 0.001% and 10% xanthan gum or gelatin derived thickeners. Suitable gelatin derived thickeners include hydroxyethyl cellulose material, and hydroxypropyl methyl cellulose.

In Table III, the stability of various alternate solutions formed using the present invention is shown. Each of the entries in Table III was prepared and diluted 100 to 1 with water. Then, each solution was individually measured for its optical density at 357 mm using a commercial ultra-violet, visible spectrophotometer. The wave length selected corresponds to the absorption maximum for chlorine dioxide. Therefore, low optical densities at this wave length reflect the stability of the solution, corresponding to the prevention of the formation of chlorine dioxide and the presence of chlorite.

TABLE III

| Example | Composition | pH | T = 60 Min. | T = 24 Hrs. |
|---|---|---|---|---|
| 1 | 0.5% $NaClO_2$ | 11 | 0.123 | 0.121 |
| 2 | 1.8% Citrate 0.6% $MgCl_2$ | 8 | 0.096 | 0.096 |

TABLE III-continued

| Example | Composition | pH | T = 60 Min. | T = 24 Hrs. |
|---------|-------------|----|-----|-----|
| 3 | 0.5% NaClO$_2$ 5.0% Urea Example 2 plus 0.8% hydroxyethyl cellulose | 8 | 0.105 | 0.105 |
| 4 | Example 2 plus 0.5% Xanthan | 8 | 0.082 | 0.105 |
| 5 | 1.8% Citrate 0.5% NaClO$_2$ 0.8% ZnCl$_2$ | 5.5 | 0.022 | 0.026 |

It has also been discovered that by employing any one of the solutions detailed in Table II, the tensile properties of the treated hair is substantially increased over the tensile properties resulting from the test sample having no post treatment. In order to effectively measure the tensile strength of the hair, an Instron Apparatus Model 1120 was used with each of the samples detailed above and the resistance forces for each of the hair fibers was determined at 20% elongation under aqueous immersion conditions. The results attained from this elongation test are shown in Table IV.

TABLE IV

| Post Treatment Composition | Force Ratio for 20% Elongation | M/mg Cysteine Hair |
|---|---|---|
| No post treatment | 0.786 | 561.6 |
| Solution A of Table II | 0.869 | 653.4 |
| Solution B of Table II | 0.885 | 874.0 |
| Solution C of Table II | 0.900 | 819.2 |

In Table IV, the values presented represent the initial reading (prior to treatment) minus the final reading (after treatment) divided by the initial reading. As a result, values closest to 1.000 indicate stronger relative tensile properties.

It has also been found that hair treated with the chlorite solution of the present invention also has the specific amino acids content which reflects less damage having been done to the hair. Typically, the term "less damage" is used to reflect the amount of cystic acid present after cosmetic treatments, as this amino acid arises from the destruction within the keratin of the disulfides, primarily formed by cystine. The application of oxidated agents to the hair following the relaxation process (chemical reduction) does not always result in the reforming of the disulfide bond, leading instead to hair fibers with markedly reduced structural integrity. The hair under these circumstances is such that the surface feels rough and weakened, as shown in Table IV.

It has been found that by employing the chlorite solution of the present invention as a post treatment, this damage is substantially reduced. In Table IV, the results achieved by employing the chlorite solution of this invention is shown with the substantially reduced damage being represented as the ratio of the value of the cysteine to the cystine. In the data provided, a value of 1,000 indicates no damage has been caused. Consequently, the closer the resulting value is to 1,000, the less was the oxidating damage to the hair. As clearly shown in Table IV, the hair fibers having the post treatment application of the chlorite solution of this invention have attained a ratio substantially closer to 1,000 than is the value attained for the hair fibers which were untreated with a chlorite solution.

Chlorite Solution as a Neutralizer

In addition to employing the chlorite solution of the present invention as a post treatment, it has also been found that the chlorite solutions can be employed either individually as the neutralizer or in combination with conventional neutralizers presently being employed in permanently waving hair. In order to prove the efficacy of the present invention, various samples of brown, blended gray and white hair were permanently waved. Each sample comprised a tress of hair of approximately 0.1 to 3 grams having an overall length of 15 centimeters. The hair samples were relaxed using conventional permanent waving solutions incorporating either an ammonium thioglycolate, a glyceryl monothioglycolate or a monoethanolamine thioglycolate. To confirm these results, permanent waving formulations, as shown in Table V, were found to provide excellent results at imparting hair relaxation.

TABLE V

| Alkaline Permanent Wave Composition | |
|---|---|
| Ammonium Thioglycolate (100%) | 15% |
| Detergent | as required |
| Fragrance | as required |
| Ammonium Hydroxide | 5.0% |
| Water deionized | q.s. to 100% |
| Acid Permanent Wave Composition | |
| Glyceryl Monothioglycolate (100%) | 15% |
| Ammonium Hydroxide | 5% |
| Detergent | as required |
| Fragrance | as required |
| Water deionized | q.s. to 100% |

After the application of the permanent wave solution, the hair samples were rinsed with tap water, followed by the application of the desired neutralizer. For purposes of comparison, some of the samples were treated with a conventional neutralizer composition containing hydrogen peroxide, such as Zotos International's Vitoxide, and with a neutralizer composition comprising sodium bromate, such as Zotos International's Design Freedom Bromate Neutralizer. With these samples serving as the control, other samples were treated with either the chlorite solutions defined in Table II as the neutralizer, the chlorite solutions of Table II in combination with ascorbic acid, or the chlorite solutions in combination with hydrogen peroxide or sodium bromate.

The results of these tests are detailed in Table VI, wherein the effectiveness of each neutralizing solution was evaluated after the hair fibers were permanently waved, as well as after six hand shampooings, 24 hour exposure to 100% humidity, and 10 hours of exposure to artificial sunlight. For the purpose of this comparative study, most of the results are given as the curl resiliency or total degree of curl which is defined by the following equation:

$$C = \frac{H_L - d}{n}$$

where $H_L$ is the total hair length
d is the distance from the root of the first curl, and
n is the total number of curls For this comparison, all of the determinations were made while the hair fibers were in the water wetted state.

In regard to determining the total change in hair color after ten hours exposure to artificial sunlight, these tests were conducted by employing a Weather-O-Meter Instrument Model 620. The results shown in Table VI, represent the change or the difference in light intensity of reflection of the hair between the initial reading and the final reading. In such measurements, a "+" indicates hair lightening, and a "−" indicates hair darkening. The data was determined using a Spectroguard Model 662.

In all of the test results provided in Table VI, the value presented represents the average obtained from numerous test samples conducted under the particular test conditions.

TABLE VI

| Permanent Wave Composition | Neutralizer | | | |
|---|---|---|---|---|
| | $H_2O_2$ | $BrO_3$ | Chlorite | Chlorite-Ascorbic Acid |
| A. Degree of Curl - Brown Hair Permanently Waved | | | | |
| Glycerolmonothioglycolate | 1.65 | 3.1 | 2.4 | 1.9 |
| Thioglycolic Acid | 1.8 | 3.0 | 2.7 | 2.3 |
| Monoethanolamine Thioglycolate | 3.2 | 2.6 | 1.9 | 2.6 |
| B. Degree of Curl - After 24 Hours at 100% Humidity | | | | |
| Glycerolmonothioglycolate | 2.1 | 2.7 | 1.9 | 2.2 |
| Thioglycolic Acid | 2.2 | 2.8 | 2.1 | 2.0 |
| Monoethanolamine Thioglycolate | 2.7 | 2.4 | 2.0 | 2.2 |
| C. Degree of Curl - After 6 Hand Shampooings | | | | |
| Glycerolmonothioglycolate | 1.9 | | 1.8 | 1.95 |
| Thioglycolic Acid | 2.1 | | 1.9 | 1.8 |
| Monoethanolamine Thioglycolate | 2.2 | 1.8 | 1.97 | — |
| D. Change in Hair Color - Exposure to Artificial Sunlight | | | | |
| Glycerolmonothioglycolate | +0.03 | | 0.00 | −0.02 |
| Thioglycolic Acid | +0.02 | | −0.03 | 0.00 |
| Thioglycolic Acid Dithiodiammonium Thioglycolate | +0.03 | | −0.01 | −0.01 |

As is apparent from the foregoing test results, the chlorite solutions of the present invention, when employed as a neutralizer, provides results at least as good as or better than typical neutralizers presently being employed in the permanent waving of hair. In addition, the chlorite solutions of the present invention are equally effective either independently or in combination with ascorbic acid.

In Table VII, the tensile strength is given for brown hair relaxed with 14% aqueous glycerol monothioglycolate at pH 8, followed by neutralization with the particular oxidant composition defined. As with one of the previous tables, the tensile strength is determined by finding the force needed to elongate the hair fiber by 20% before treatment, subtracting from this value the 20% elongation value resulting after treatment and dividing the remainder by the initial value. As a result, values nearest to 1.000 indicate stronger relative tensile properties.

TABLE VII

| Test | Neutralizer | Relative Force at 20% Elongation |
|---|---|---|
| 1 | 2% $H_2O_2$ | 0.805 |
| 2 | 0.6% $ClO_2$ 1.8% Citrate 0.8% $MgCl_2$ | 0.885 |
| 3 | 0.6% $ClO_2$ 1.8 Citrate 0.8% $MgCl_2$ 2.0% Ascorbic Acid | 0.862 |
| 4 | 10% $BrO_3$ | 0.785 |
| 5 | 1:1 ratio of 2% $H_2O_2$ and solution in test 2 | 0.857 |
| 6 | 1:1 ratio of 10% $BrO_3$ and solution in test 2 | 0.825 |

In order to provide a chlorite solution incorporating ascorbic acid, 100 milliliters of any of the solutions defined in Table II is combined with 2 grams of ascorbic acid for dissolution therein. In this simple, straight-forward manner, an effective combination of the chlorite solution and ascorbic acid is attained.

If desired, the following alternative process can be employed in order to attain a combined ascorbic acid-chlorite solution incorporating hair conditioners to further condition the hair during the neutralization step of the process. In this formulation, 2 grams of ascorbic acid are dissolved in a separate container in 4 to 25 grams of propylene or ethylene glycol containing between 0.01 and 3 grams of water. In addition, between about 0.001% and 2% of conditioners are added to the solution. Although various conditioners can be employed, the preferred conditioners include ascorbyl palmitate, alkyldimethylsiloxanes, cyclomethicones, and dimethicone copolyols.

The resulting mixture is then added to any of the chlorite solutions defined in Table II at a dilution of one part of the ascorbic acid mixture to between about 30 to 100 parts of the chlorite solution. The resulting mixture is then shaken until thoroughly mixed prior to application to the hair.

As is particularly apparent from the results provided in Table VII, the commonly used neutralizer, sodium bromate, may also be mixed with the chlorite containing solutions of the present invention to effect the neutralization step in a permanent waving process. By employing this combination, it has been found that not only did the hair develop a durable curl, equal to that observed with the bromate alone, but the resulting curl was more durable to such cosmetic after treatments as shampooing and combing. It was also observed that the mal-odor associated with using monoethanolamine thioglycolate was effectively eliminated.

One formulation for attaining a bromate and chlorite solution in accordance with this invention is to dissolve between about 4 and 24 g of an alkali metal, an ammonium, or phosphonium salt of bromate in water or water and an alcohol having a carbon length of between $C_2$ and $C_{10}$ and a hydroxylic content of between 1 and 15. Additionally, it is desirable to also mix urea into the solution at sufficient concentration to maintain a bromate:urea ratio of between 0.5 and 2. Finally, any one of the chlorite solutions detailed in Table II is mixed therewith at a volume to volume ratio of between 0.5 and 2, immediately prior to use.

Concentrated Chlorite Solutions and Buffering Mediums

Depending upon the final concentration, a 0.1% to 20% by weight solution of sodium chlorite has a pH ranging between 9.9 and 11.2. When kept free from oxygen and light, the solutions are moderately stable, however, the high degree of alkalanity could be deleterious to the hair. In addition, when attempts have been made to lower the pH of the solution, so as to be more equivalent to the pH commonly employed with both peroxide and bromate containing neutralizing compositions, the immediate degradation of the chlorite to chlorine and chlorine dioxide gases was found to occur.

However, it has now been found that solutions of sodium chlorite can be maintained independently in an amber, opaque, or completely pigmented bottle for extended time periods with complete stability provided the concentration of sodium chlorite ranges between 0.01% and 20% by weight. When needed for application to the hair, these solutions can be mixed immediately prior to use with the remaining components defined in Table II in order to attain the previously described stable chlorite/citrate/divalent metal ion composition of the present invention for use at a pH of 4.5 to 7.5. In this way, long term, safe storage of the chlorite solutions of this invention are assured and a highly effective hair application is realized.

In Table VIII, Table IX and Table X, three alternate formulations are provided for attaining a stable, two-part, sodium chlorite composition which can be maintained for extended time periods and intermixed prior to use to attain the desired sodium chlorite solution for use in accordance with the present invention.

TABLE VIII

|  | % (By Weight) |
|---|---|
| Part A | |
| Sodium Citrate | 6.0% |
| Zinc Chloride | 2.0% |
| Urea | 2.0% |
| Cellulose Gum | 0.2% |
| Water | q.s. to 100% |
| Part B | |
| Sodium Chlorite (5% solution) | 1.0% |

TABLE IX

|  | % (By Weight) |
|---|---|
| Part A | |
| Sodium Citrate | 6.0% |
| Zinc Chloride | 2.0% |
| Magnesium Chloride | 1.0% |
| Urea | 2.0% |
| Cellulose Gum | 0.2% |
| Water | q.s. to 100% |
| Part B | |
| Sodium Chlorite (20% solution) | 4.0% |

TABLE X

|  | % (By Weight) |
|---|---|
| Part A | |
| Sodium Citrate | 6.0% |
| Magnesium Citrate | 3.0% |
| Zinc Chloride | 2.0% |
| Urea | 2.0% |
| Cellulose Gum | 0.2% |
| Water | q.s. to 100% |
| Part B | |
| Sodium Chlorite (10% solution) | 24.0% |

It will thus be seen that the objects set forth above, among those made apparent from the preceding description are efficiently attained and, since certain changes may be made in carrying out the above process and in the composition set forth without departing from the scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

Having described our invention, what we claim as new and desire to secure by Letters Patent is:

1. A composition for application to hair as part of a permanent waving process, said composition comprising:
   A. between about 0.001% and 10% by weight of a chlorite salt;
   B. between about 0.01% and 20% by weight of an organic or inorganic buffer salt having a pH ranging between about 3.0 and 6.5;
   C. between about 0.001% and 10% by weight of a divalent metal ion; and
   D. water forming the balance;
   whereby the application of said composition to the hair substantially improves the resulting curl retention and condition of the final permanently waved hair.

2. The composition defined in claim 1, wherein the aqueous chlorite solution comprises an alkali metal, ammonium, or organo ammonium chlorite salt.

3. The composition defined in claim 2, wherein said chlorite salt is further defined as comprising sodium chlorite.

4. The composition defined in claim 1, wherein said organic or inorganic buffer salt is further defined as comprising the alkali metal salts of one selected from the group consisting of citric acid, tartaric acid, ethylene tetra-acetoxylamine and acetylacetone.

5. The composition defined in claim 1, wherein said divalent metal ion is further defined as comprising one selected from the group consisting of zinc, copper, magnesium, and manganese.

6. The composition defined in claim 1, wherein said composition is further defined as comprising:
   A. between about 0.4% and 6% by weight sodium chlorite,
   B. between about 1.2% and 12% by weight of the organic or inorganic buffer salt, and
   C. between about 0.6% and 10% by weight of the divalent metal ion.

7. The composition defined in claim 6, wherein said buffer salt is further defined as comprising one selected from the group consisting of tribasic sodium citrate and a magnesium citrate, and the divalent metal ion is further defined as comprising a water soluble salt of a divalent metal ion selected from the group consisting of magnesium sulfate, magnesium chloride, copper sulfate, magnesium chloride hexahydrate, copper chloride, zinc chloride hydrate, zinc sulfate, and zinc chloride.

8. The composition defined in claim 1, wherein said composition is further defined as being applied to the hair as a post treatment immediately after the application of both a reducing agent and an oxidizing agent to permanently wave the hair.

9. The composition defined in claim 1, wherein said composition is applied to the hair as a neutralizing or oxidizing mixture employed during the permanent waving process for the hair.

10. The composition defined in claim 9, Wherein said composition is further defined as being intermixed with an oxidizer selected from the group consisting of hydrogen peroxide, and alkali metal and ammonium salts of bromate, persulfate and carbonate.

11. The composition defined in claim 1, wherein said composition further comprises
   E. between about 0.1% and 8% by weight of urea.

12. The composition defined in claim 1, wherein said composition is further defined as comprising
   E. between about 0.001% and 10% by weight of one or more selected from the group consisting of xanthan gum, hydroxyethyl cellulose and hydroxypropyl methyl cellulose.

13. The composition defined in claim 1, wherein said composition is further defined as comprising
   E. between about 0.01% and 5% by weight of ascorbic acid.

14. The composition defined in claim 13, wherein the composition is further defined as comprising
   F. between about 0.02% and 10% by weight of one selected from the group consisting of propylene glycol and ethylene glycol.

15. The composition defined in claim 14, wherein the composition is further defined as comprising
   G. between about 0.001% and 2% by weight of at least one conditioner selected from the group consisting of ascorbyl palmitate, alkyldimethylsiloxanes, cyclomethicones and dimethicone copolyols.

16. A two-part composition for providing long-lasting, safe storage of aqueous sodium chlorite, said composition comprising two separate and independently stored component parts, said first component part comprising aqueous sodium chlorite having a concentration of between about 0.01% and by weight, and said second component part comprising
   A. between about 0.01% and 10% by weight of at least one selected from the group consisting of sodium citrate and magnesium citrate;
   B. between about 0.5% and 5% by weight/volume of at least one selected from the group consisting of zinc chloride and magnesium chloride;
   C. between about 0.1% and 8% by weight of urea; and
   D. between about 0.05% and 1% by weight of a cellulose gel; and
   E. water forming the balance.

17. The two-part composition defined in claim 16, wherein said first component part of aqueous sodium chlorite is further defined as being stored in a completely pigmented bottle.

18. The two-part composition defined in claim 16, wherein said final composition comprises a pH ranging between about 3.5 and 9.0 when said two component parts forming the composition are intermixed with each other.

19. A composition for application to the hair as part of a permanent waving process, said composition comprising:
   A. between about 0.2% and 2.2% by weight of sodium chlorite;
   B. between about 0.5% and 5% by weight of tribasic sodium citrate;
   C. between about 0.3% and 2.0% by weight of a water soluble salt of a divalent metal ion selected from the group consisting of magnesium sulfate, magnesium chloride, copper sulfate, copper chloride, magnesium chloride hexahydrate, zinc chloride hydrate; zinc sulfate and zinc chloride; and
   D. water forming the balance.

20. The composition defined in claim 19 wherein said composition is further defined as being intermixed with an oxidizer selected from the group consisting of hydrogen peroxide and alkali metal and ammonium salts of bromate, persulfate and carbonate.

21. A process for permanently waving hair by performing the conventional steps to reduce the hair and to rinse the reducing solution from the hair, followed by the steps of:
   A. saturating the reduced hair with an oxidizer comprising
      a. between about 0.001% and 8% by weight of a chlorite salt;
      b. between about 0.01% and 20% by weight of an organic or inorganic buffer salt having a pH ranging between about 3.0 and 6.5;
      c. between about 0.001% and 10% by weight of a divalent metal ion; and
   B. rinsing the oxidizer from the hair.

22. The process defined in claim 21, wherein said oxidizer is further defined as being combined with one selected from the group consisting of hydrogen peroxide and alkali metal and ammonium salts of bromate, persulfate, and carbonate, and thoroughly mixed therewith prior to being applied to the hair.

23. A process for permanently waving hair by performing the conventional steps for reducing and oxidizing the hair, followed by the additional step of:
   A. applying a post treatment solution to the freshly permanently waved hair, such solution comprising
      a. between about 0.001% and 8% by weight of a chlorite salt;
      b. between about 0.01% and 20% by weight of an organic or inorganic buffer salt having a pH ranging between about 3.0 and 6.5;
      c. between about 0.001% and 10% by weight of a divalent metal ion; and
      d. water forming the balance.

* * * * *